United States Patent
Yu et al.

(10) Patent No.: US 10,429,243 B2
(45) Date of Patent: Oct. 1, 2019

(54) SPACE-BASED SODIUM LIDAR INSTRUMENT AND METHOD OF OPERATION

(71) Applicant: U.S.A. as represented by the Administrator of the National Aeronautics and Space Administration, Washington, DC (US)

(72) Inventors: Anthony W. Yu, Spencerville, MD (US); Michael A. Krainak, Fulton, MD (US); Diego Janches, Tracys Landing, MD (US); Sarah L. Jones, Bowie, MD (US); Branimir Blagojevic, Ellicott City, MD (US)

(73) Assignee: U.S.A. as represented by the Administrator of the National Aeronautics and Space Administration, Washington, DC (US)

( * ) Notice: Subject to any disclaimer, the term of this patent is extended or adjusted under 35 U.S.C. 154(b) by 437 days.

(21) Appl. No.: 15/246,870

(22) Filed: Aug. 25, 2016

(65) Prior Publication Data
US 2018/0058935 A1    Mar. 1, 2018

(51) Int. Cl.
*H01S 3/00* (2006.01)
*G01J 5/10* (2006.01)
(Continued)

(52) U.S. Cl.
CPC .............. *G01J 5/10* (2013.01); *G01N 21/39* (2013.01); *G01S 7/4814* (2013.01); *G01S 17/102* (2013.01); *G01S 17/95* (2013.01); *H01S 3/0085* (2013.01); *H01S 3/042* (2013.01); *H01S 3/0405* (2013.01); *H01S 3/0602* (2013.01); *H01S 3/0606* (2013.01); *H01S 3/08095* (2013.01); *H01S 3/0941* (2013.01); *H01S 3/108* (2013.01); *H01S 3/10092* (2013.01); *H01S 3/117* (2013.01); *H01S 3/1611* (2013.01);
(Continued)

(58) Field of Classification Search
CPC .... H01S 3/091; H01S 3/10084; H01S 3/1618; H01S 3/1617; H01S 3/1673; H01S 3/30
USPC ........................................................ 359/334
See application file for complete search history.

(56) References Cited

U.S. PATENT DOCUMENTS

| | | | |
|---|---|---|---|
| 9,570,882 B2 * | 2/2017 | Spiekermann | H01S 3/09415 |
| 2006/0268950 A1 * | 11/2006 | Kane | H01S 3/10092 372/30 |

* cited by examiner

*Primary Examiner* — Mark Hellner
(74) *Attorney, Agent, or Firm* — Christopher O. Edwards; Bryan A. Geurts; Mark P. Dvorscak

(57) ABSTRACT

The present invention relates an apparatus and method for measuring range-resolved atmospheric sodium temperature profiles using a space-based Lidar instrument, including a diode-pumped Q-switched self-Raman c-cut Nd:YVO$_4$ laser with intra-cavity frequency doubling that could produce multi-watt 589 nm wavelength output. The c-cut Nd:YVO$_4$ laser has a fundamental wavelength that is tunable from 1063-1067 nm. A continuous wave narrow linewidth diode laser is used as an injection seeder to provide single-frequency grating tunable output around 1066 nm. The injection-seeded self-Raman shifted Nd:VO$_4$ laser is tuned across the sodium vapor D$_2$ line at 589 nm. In one embodiment, a space-qualified frequency-doubled 9 Watt at 532 nm wavelength Nd:YVO$_4$ laser, is utilized with a tandem interference filter temperature-stabilized fused-silica-etalon receiver and high-bandwidth photon-counting detectors.

19 Claims, 2 Drawing Sheets

(51) Int. Cl.
  *H01S 3/0941* (2006.01)
  *H01S 3/16* (2006.01)
  *H01S 3/08* (2006.01)
  *H01S 3/06* (2006.01)
  *H01S 3/117* (2006.01)
  *H01S 3/04* (2006.01)
  *G01N 21/39* (2006.01)
  *G01S 17/10* (2006.01)
  *G01S 17/95* (2006.01)
  *G01S 7/481* (2006.01)
  *H01S 3/10* (2006.01)
  *H01S 3/108* (2006.01)
  *H01S 3/042* (2006.01)
  *H01S 3/109* (2006.01)
  *H01S 3/13* (2006.01)
  *G01N 21/17* (2006.01)

(52) U.S. Cl.
  CPC .... *H01S 3/1673* (2013.01); *G01N 2021/1793* (2013.01); *G01N 2021/399* (2013.01); *G01N 2201/068* (2013.01); *H01S 3/109* (2013.01); *H01S 3/1303* (2013.01); *Y02A 90/19* (2018.01)

SPACE-BASED SODIUM LIDAR INSTRUMENT AND METHOD OF OPERATION

BACKGROUND OF THE INVENTION

1. Field of the Invention

The present invention relates to a Lidar instrument including a laser transmitter, which remotely measures the sodium (Na) layer and the composition and dynamics of Earth's mesosphere.

2. Description of the Related Art

Layers of neutral metal atoms, such as Iron (Fe), Magnesium (Mg), Calcium (Ca), Potassium (K) and Sodium (Na), which peak between 85 and 95 km and are about 20 kilometers (km) in width, are produced by the daily ablation of billions of Interplanetary Dust Particles (IDPs). As these metallic species are ionized during ablation, by sunlight's ultraviolet photons, or by charge exchange with existing atmospheric ions, meteoroids affect the structure, chemistry, dynamics, and energetics of the mesospheric and lower thermosphere (MLT). The strong optical signals that some of these metal layers produce, in particular the Na layer, provides information on the composition, temperature and winds of the MLT making them an optimal tracer of atmospheric dynamics and circulation, and potentially enabling the measurement of quantities that are important to address several compelling scientific questions related to the Earth's upper atmosphere and the geospace environment.

Specifically, gravity waves (GWs) having wavelengths smaller than a few hundred km are the dominant contributors to momentum transport and deposition in the MLT, which largely drive the global circulation and thermal structure and interactions with the tides and planetary waves in this region. Thus, predicting the impact on atmospheric chemistry and dynamics is a major uncertainty in current atmospheric models.

Accordingly, there is a pressing need to be able to perform high-resolution measurements that can be used to characterize small-scale dynamics (i.e., gravity waves with wavelengths smaller than a few hundred km) and their effects in the MLT on a global basis. Although it is believed that these small-scale dynamics are dominant contributors to momentum transport and deposition in the MLT, which largely drive the global circulation and thermal structure and interactions with tides and planetary waves in this region, there is currently no method or instrument to measure these dynamics.

Further, such an instrument should be able to take measurements which are highly resolved, in space and time, of global temperature and wind profiles, as well as the global distribution of GWs (e.g., different orographic forcing sources) and their spectra, which will add to the understanding of key indicators of radiative cooling in the mesosphere.

Remote-sensing satellites have obtained the first global characterization of the basic structure of the MLT region in terms of large-scale temperature and wind climatologies, resulting in a much richer picture of the structure and variability of the mesosphere. Although these measurements have shown the high temporal variability of both the zonal mean state as well as large scale organized perturbations, such as planetary waves and atmospheric tides, they failed at providing information required for the fundamental characterization of how the basic state is established and maintained.

Although ground-based and airborne Na and Fe Lidar observations have demonstrated that these techniques are ideal to obtain high-resolution measurements of these quantities, and these Lidars provide very high temporal and vertical resolutions measurements, the ground-based sites are geographically sparse and cannot provide representative global climatologies.

Recent models of the mesospheric Na layer have shown large variations in the Na constituents over timescales from days to months. These studies also demonstrated that measuring the Na layer at a global scale can enable the study of how external sources impact this region. For example, the short-term response of the upper atmosphere to a stratospheric sudden warming is clearly revealed in the Na column. Further, seasonality of Na constituents is strongly affected by variations in the meteor input function (MIF) and transport via the mean meridional wind.

Accordingly, a space-borne remote sensing technique that will enable acquisition of global sodium density, temperature and wind measurements in the MLT with the spatial and temporal resolution required to resolve issues associate with the structure, chemistry, dynamics, and energetics of this region, is needed.

SUMMARY OF THE INVENTION

The present invention relates to a space-borne remote sensing technique that enables the acquisition of global sodium (Na) density, temperature, and wind measurements in the mesospheric and lower thermosphere (MLT), with the spatial and temporal resolution required to resolve issues associated with the structure, chemistry, dynamics, and energetics of the MLT region. In one embodiment, the present invention relates to a Lidar instrument including a laser transmitter, which remotely measures the sodium (Na) layer and the composition and dynamics of Earth's mesosphere.

In one embodiment, the present invention is related to a laser transmitter that is capable of global high-resolution measurements of the Na layer using resonance fluorescence Lidar, which will permit, not only measurements of zonal mean structures, planetary waves and tides, but also uniquely characterize the global distribution of gravity waves (GWs). Such measuring capabilities will enable more accurate constraints of global circulation models (GCMs) via GW drag parameterization enabled by the global estimation GW forcing and transport. Additionally, measuring the global distribution and variability of meteoric Na will enable constraint of models of the MLT chemistry, meteoroid ablation and mass loss processes, and zodiacal dust cloud, as well as their impact in planetary atmospheres.

In one embodiment, the present invention includes a zenith pointing Na Doppler Lidar which provides measurements of vertical profiles of absolute temperature, absolute Na density and vertical wind perturbations. These data enable the global characterization of the mesopause region temperature and Na density structure as well as gravity wave (GW) variances and spectra. In addition, the present invention characterizes the wave-induced vertical transport of Na and other mesopause region species, by computing the vertical Na flux profiles, and also in one embodiment, the heat flux profiles.

In one embodiment, the laser of the present invention is a diode-pumped Q-switched self-Raman c-cut Nd:YVO$_4$ laser with intra-cavity frequency doubling that could produce multi-watt 589 nm wavelength output. The c-cut Nd:YVO$_4$ laser has a fundamental wavelength that is tunable from 1063-1067 nm. A continuous wave (CW) narrow linewidth laser (i.e., an external cavity diode laser) is used as an injection seeder to provide single-frequency grating tunable output around 1066 nm. The injection-seeded self-Raman shifted Nd:YVO$_4$ laser is tuned across the sodium vapor D$_2$ line at 589 nm. In one embodiment, a space-qualified frequency-doubled 9 Watt at 532 nm wavelength Nd:YVO$_4$ laser, is utilized with a tandem interference filter temperature-stabilized fused-silica-etalon receiver and high-bandwidth photon-counting detectors.

In one embodiment, a Lidar instrument includes: a laser transmitter including: a continuous wave diode laser which emits laser beams at an 808/880 nm (or 885 nm or 914 nm) wavelength, through mode matching lenses and a high reflective mirror to a c-cut Nd:YVO$_4$ crystal; a tunable seed continuous wave diode laser which emits laser beams through a plurality of mode matching lens, the laser beams which are redirected by a beam splitter to the c-cut Nd:YVO$_4$ crystal, and which produces light at a wavelength of 1066 nm; wherein the tunable laser light after passing through the c-cut Nd:YVO$_4$ crystal self-Raman shifts to 1178 nm; wherein the continuous wave diode laser and the tunable seed continuous wave diode laser produce tunable laser light across the sodium D$_2$ absorption line; and wherein the c-cut Nd:YVO$_4$ crystal is a zig-zag crystal which supports multiple total internal reflections of optical wave propagation therethrough, and increases an optical path length greater than a physical dimension of the zig-zag crystal.

In one embodiment, the tunable laser light, after passing through the c-cut Nd:YVO$_4$ crystal, passes through one of a lithium triborate (LBO) crystal or a potassium titanyl phosphate (KTP) crystal, or other appropriately chosen crystal, which performs intra-cavity frequency doubling to output tunable laser light at 589 nm.

In one embodiment, the Lidar instrument further includes: an output coupler, operating at 1066 nm wavelength, through which the tunable laser light passes after passing through one of the lithium triborate crystal or the potassium titanyl phosphate crystal, and which outputs the tunable laser light at 589 nm wavelength.

In one embodiment, the Lidar instrument further includes: an acousto-optic Q-switch which produces high-peak-power pulses to assist in the self-Raman shift to the 1178 nm wavelength in the c-cut Nd:YVO$_4$ crystal.

In one embodiment, a tuning range for a Na fluorescence spectrum is 4 GHz. 1. In one embodiment, the c-cut Nd:YVO$_4$ crystal is wrapped with an indium foil and bonded to a thermoelectric cooler (TEC) using a thermal phase-change material (TPCM) as interface between the indium foil wrapped crystal and the TEC, for efficient cooling and thermal management.

In one embodiment, the zig-zag crystal is an even bounced vanadate slab that exhibits 10 mrad pyramidal error, and exhibits lasing pulses of 50 Hz, at 100 μs pump duration, and Q-switched lasing with Cr$^{4+}$:YAG as a saturable absorber.

In one embodiment, the zig zag crystal is prepared from two pieces of vanadate crystals that are diffusion bonded end-to-end to achieve a length of 40 nm.

In one embodiment, the diffusion bonding process is performed such that the crystalline axes are aligned to less than ±2 mrad.

In one embodiment, remote atmospheric spectroscopy is performed by using the continuous wave diode laser as a master laser diode, the master laser diode including: a tunable Distributed FeedBack laser diode at 1178.4 nm, that is doubled to 589 nm and wavelength-locked to the sodium D$_2$ absorption line.

In one embodiment, the tunable continuous wave diode laser is a slave laser diode dynamically offset-locked to the master laser diode by using an optical phase-locked loop.

In one embodiment, the Lidar instrument further includes: a Mach-Zehnder modulator; and an amplifier; wherein pulses from the slave laser diode are externally modulated by the Mach-Zehnder modulator to form a frequency-stepped pulse train which is amplified by the amplifier; and wherein the amplified frequency-stepped pulse train is used to repeatedly measure at multiple points across the sodium D$_2$ absorption line.

In one embodiment, the Lidar instrument further includes: a detector used as a full-spectroscopic sodium lineshape waveform to recover mesospheric temperature profiles.

In one embodiment, a method of measuring range-resolved atmospheric sodium temperature profiles using a space-based Lidar instrument, includes: providing a continuous wave diode laser which emits laser beams at a predetermined wavelength through mode matching lenses and a high reflective mirror to pump a c-cut Nd:YVO$_4$ crystal; providing a tunable seed continuous wave diode laser which emits laser beams through a plurality of mode matching lenses; redirecting the laser beams emitted from the tunable seed continuous wave diode laser using a beam splitter, to the c-cut Nd:YVO$_4$ crystal, and which tunes the continuous wave diode laser to produce light at a wavelength of 1066 nm; self-Raman shifting the tunable laser light after passing through the c-cut Nd:YVO$_4$ crystal, to 1178 nm; wherein the continuous wave diode laser and the tunable seed continuous wave diode laser produce tunable laser light across the sodium D$_2$ absorption line; and wherein the c-cut Nd:YVO$_4$ crystal, is a zig-zag crystal, said zig-zag crystal supporting multiple total internal reflections of optical wave propagation therethrough, and increasing an optical path length greater than a physical dimension of the zig-zag crystal.

In one embodiment, the method further includes: passing the tunable laser light through the c-cut Nd:YVO$_4$ crystal and then one of a lithium triborate (LBO) crystal or a potassium titanyl phosphate (KTP) crystal, in order to perform intra-cavity frequency doubling to output tunable laser light at 589 nm from an output coupler operating at 1066 nm wavelength.

In one embodiment, the method further includes: preparing the zig zag crystal from two pieces of vanadate crystals that are diffusion bonded end-to-end to achieve a length of 40 nm; and performing the diffusion bonding process such that the crystalline axes are aligned to less than ±2 mrad.

In one embodiment, the method further includes: performing remote atmospheric spectroscopy using the continuous wave diode laser as a master laser diode, the master laser diode; wherein a tunable Distributed FeedBack laser diode at 1178.4 nm, is doubled to 589 nm and wavelength-locked to a sodium D$_2$ absorption line; and wherein the tunable continuous wave diode laser is a slave laser diode dynamically offset-locked to the master laser diode by using an optical phase-locked loop.

In one embodiment, the method further includes: externally modulating pulses from the slave laser diode using a Mach-Zehnder modulator to form a frequency-stepped pulse train which is amplified by the amplifier; and measuring repeatedly, using the amplified frequency-stepped pulse train, multiple points across the sodium absorption line.

In one embodiment, the method further includes: using a detector as a full-spectroscopic sodium lineshape waveform to recover mesospheric temperature profiles.

Thus has been outlined, some features consistent with the present invention in order that the detailed description thereof that follows may be better understood, and in order that the present contribution to the art may be better appreciated. There are, of course, additional features consistent with the present invention that will be described below and which will form the subject matter of the claims appended hereto.

In this respect, before explaining at least one embodiment consistent with the present invention in detail, it is to be understood that the invention is not limited in its application to the details of construction and to the arrangements of the components set forth in the following description or illustrated in the drawings. Methods and apparatuses consistent with the present invention are capable of other embodiments and of being practiced and carried out in various ways. Also, it is to be understood that the phraseology and terminology employed herein, as well as the abstract included below, are for the purpose of description and should not be regarded as limiting.

As such, those skilled in the art will appreciate that the conception upon which this disclosure is based may readily be utilized as a basis for the designing of other structures, methods and systems for carrying out the several purposes of the present invention. It is important, therefore, that the claims be regarded as including such equivalent constructions insofar as they do not depart from the spirit and scope of the methods and apparatuses consistent with the present invention.

DESCRIPTION OF THE INVENTION

Figure 1:
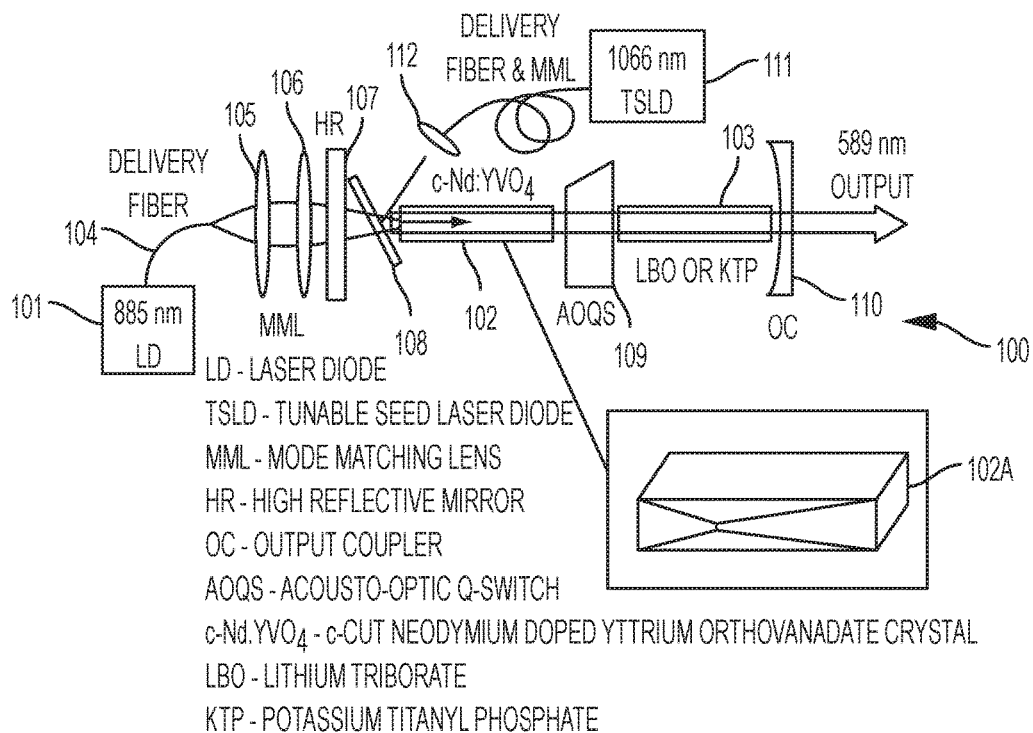
FIG. 1 is a schematic diagram of a Na Lidar injection-seeded c-Nd:YVO$_4$ laser transmitter of a Lidar instrument, according to one embodiment consistent with the present invention.

The present invention relates to a space-borne remote sensing technique that enables the acquisition of global sodium (Na) density, temperature, and wind measurements in the mesospheric and lower thermosphere (MLT), with the spatial and temporal resolution required to resolve issues associated with the structure, chemistry, dynamics, and energetics of the MLT region. In one embodiment, the present invention relates to a Lidar instrument including a laser transmitter to remotely measure the Na layer and the composition and dynamics of Earth's mesosphere.

In one embodiment, the present invention is related to a laser transmitter that is capable of global high-resolution measurements of the Na layer using resonance fluorescence Lidar, which will permit, not only measurements of zonal mean structures, planetary waves and tides, but also uniquely characterize the global distribution of gravity waves (GWs). Such measuring capabilities will enable more accurate constraints of global circulation models (GCMs) via GW drag parameterization enabled by the global estimation GW forcing and transport. Additionally, measuring the global distribution and variability of meteoric Na will enable constraint of models of the MLT chemistry, meteoroid ablation and mass loss processes, and zodiacal dust cloud, as well as their impact in planetary atmospheres.

In one embodiment, the present invention includes a zenith pointing Na Doppler Lidar which provides measurements of vertical profiles of absolute temperature, absolute Na density and vertical wind perturbations. These data enable the global characterization of the mesopause region temperature and Na density structure as well as gravity wave (GW) variances and spectra. In addition, the present invention characterizes the wave-induced vertical transport of Na and other mesopause region species, by computing the vertical Na flux profiles, and also in one embodiment, the heat flux profiles.

Vertical constituent transport by gravity waves (GWs) plays a crucial role in mesopause region chemistry which establishes the structure and seasonal variations of key species such as odd-oxygen. By restricting wind observations to the vertical wind perturbation profiles, rather than absolute winds, the nadir pointing accuracy and stability of the instrument can be relaxed.

In one embodiment, two beams point off zenith in an orthogonal configuration, and one beam points zenith, so that temperature, vector wind and Na density can be measured simultaneously and globally with very high resolution and accuracy. This further enhances the scientific benefits of the present invention, including the direct measurements of gravity wave (GW) momentum flux.

In one embodiment, the present invention is used to measure range-resolved atmospheric-sodium-temperature profiles from low-Earth-orbit (LEO) using a space-based Lidar. The atmospheric temperature is deduced from the linewidth of the resonant fluorescence from the atomic sodium vapor D$_2$ (Fraunhofer) absorption line as measured by a tunable laser.

In one embodiment, the Na Lidar of the present invention includes a laser transmitter, which has the following specifications.

TABLE 1

| | |
|---|---|
| Wavelength (nm) | 589.2 nm ± 0.3 nm |
| Optical Power (@589 nm) | 9 W |
| Pulsed | Yes |
| Wall-plug efficiency | >2% |
| Pulse width | 1-50 ns |
| Spectral width | <100 MHz |
| Tuning range | 0.5 nm |
| Tuning speed | <10 microseconds per GHz |
| Beam Quality (M^2) | <4 |
| Spaceflight heritage | Yes |

FIG. 1 shows one embodiment of a Na Lidar injection-seeded c-cut neodymium-doped yttrium orthovanadate crystal (c-Nd:YVO$_4$) laser transmitter 100 of the present invention. In one embodiment, as shown in FIG. 1, an 808/880 nm (or suitable wavelength, such as 885 nm, or 914 nm) continuous wave (CW) diode laser 101 is coupled to fiber 104, and emits laser beams through mode matching lenses (MML) 105-106, a high reflective mirror 107, and a beam splitter 108, to pump or excite the atoms in a 0.3 at-% Nd$^{3+}$ doped c-cut Nd:YVO$_4$ crystal 102, creating a population inversion inside the crystal to allow lasing at 1066 nm. In one embodiment, the c-cut Nd:YVO$_4$ crystal 102 has dimensions of 3 mm×3 mm×20 mm, and produces tunable laser light from 1062.2-1066.7 nm (rather than the a-cut crystal, which lases at 1064 nm).

In one embodiment, a tunable seed CW narrow linewidth (i.e., external cavity) laser diode (TSLD) 111 is coupled to fiber 112, and laser beams from the laser 111 pass through mode matching lens (MML) 112, and are redirected by beam splitter 108 to the Nd:YVO$_4$ crystal 102, such that the TSLD 111 acts as an injection seeder for the Nd:YVO$_4$ laser to allow for tuning of the Nd:YVO$_4$ laser at the fundamental wavelength of 1066 nm.

In one embodiment, after the beams from laser 101 pass through crystal 102, the wavelength self-Raman shifts to 1178 nm, followed by intra-cavity frequency doubling with a lithium triborate (LBO) or potassium titanyl phosphate (KTP) crystal 103 (or other appropriately chosen crystal), to generate about 0.5 W of average power, to pass through output coupler (OC) 110, and output a beam at 589 nm wavelength. The output coupler 110 operates in CW and only in the 1066 nm fundamental wavelength, and the laser output 101 is tuned using a 1 mm thick fused-silica intra-cavity etalon (lenses 105-106), over about 5 nm.

In one embodiment, the KTP 103 is also bonded to a temperature controller for temperature control for type II critical phase matching at 300° K. The 1066 nm and the 1178 nm wavelengths leak out of the laser cavity and travel collinearly with the 589 nm output beam.

In one embodiment, the above laser transmitter operation is accomplished by use of an active acousto-optic Q-switch (AOQS) 109, which produces high-peak-power pulses to exploit the non-linear self-Raman shift to 1178 nm wavelength in the crystal 102. The Q-switching provides the time-of-flight pulses for range-resolved atmospheric temperature measurements while also increasing the intra-cavity frequency-doubling efficiency for 589 nm wavelength output generation. The tunable injection seeding 1066 nm wavelength diode laser 101 allows tuning of the Nd:YVO$_4$ laser 100 to (and across) the exact Na D$_2$ line. The injection seeding allows rapid all-electronic wavelength tuning.

In one embodiment, the tuning range needed to profile the entire Na fluorescence spectrum is 4 GHz. The equivalent wavelength range at 589 nm for this 4 GHz frequency range is 4.6 pm. The injection seed laser 101 is wavelength-locked to an absolute wavelength to within 4 MHz of the center of the D$_2$ lines, then using injection current, the laser 101 is tuned over the ±2 GHz (±2.3 pm) range to profile the Na spectrum.

In one embodiment, the laser crystal 102 is wrapped with an indium foil and bonded to a thermoelectric cooler (TEC), but with a novel thermal phase-change material (TPCM) disposed between the indium foil and the TEC for a bonding purpose, and for efficient cooling and thermal management. This allows for better thermal conduction than epoxies.

A thermistor located on the side of the laser crystal 102 is used to measure the crystal 102 surface temperature and provide feedback to the temperature feedback loop to maintain the laser crystal 102 to 20° C.

In one embodiment, the 880 nm (for example) laser 101 was used for direct pumping the $^4F_{3/2}$ level of the c-Nd:YVO$_4$ crystal 102 to further reduce the quantum defect. The quantum defect for a given laser transition is determined by the difference between the pump and lasing wavelengths. The laser performance, heat generation and efficiency could be improved by reducing this defect.

In one embodiment, a zig-zag c-Nd:YVO$_4$ slab crystal 102A (see FIG. 1) and pump diodes were used for power scaling the Q-switched self-Raman vanadate laser 100. The zig-zag slab crystal 102A is pumped by the quasi-CW laser diode 101 array at 808/880 nm. The zig-zag slab crystal 102A is an even bounced vanadate slab that supports multiple total internal reflections of optical wave propagation therethrough. The zig-zag geometry allows for a much longer optical path length than the physical slab dimension. The zig-zag slab crystal 102A shows minimal pyramidal error (about 10 mrad), and exhibits long lasing pulses (50 Hz, 100 μs pump duration), and Q-switched lasing with Cr$^{4+}$:YAG as a saturable absorber.

In one embodiment, the zig-zag slab crystal 102A of the laser 100 of the present invention, is prepared from two pieces of vanadate crystals that are diffusion bonded end-to-end to achieve the required length. In one embodiment, the tip-to-tip dimension is about 40 nm. Since the crystalline axes are an important parameter in the laser 100 design, the diffusion bonding process is performed such that the crystalline axes are aligned to less than ±2 mrad.

Figure 2:
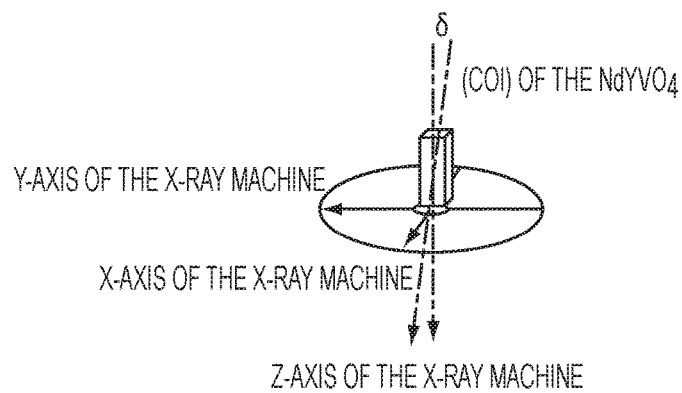
FIG. 2 is a diagram showing the axes measured, of the laser transmitter of FIG. 1, according to one embodiment consistent with the present invention.

In one embodiment, to ensure the crystalline axes are aligned as required, the samples are inspected and verified prior to the diffusion bonding process. The crystal sample is clamped between a precision V-block and a regular precision block, and the two side walls of the crystal blanks are used as a reference. The c-plane does not touch the X-ray surface flat, and the angles measured are shown in FIG. 2.

In one embodiment, both pairs of the crystal blanks side walls were used as reference planes and the deviation of crystal c-axis to the X-ray machine Z-axis, and angle δ were measured. The side walls were used as a reference for polishing the end faces for bonding.

In one embodiment, each sample was measured five times with each pair of side walls as a reference. The results confirmed that the c-axes of two of the three Nd:YVO$_4$ samples prepared, are within 0.1°, and the third was at about 0.1°. The results confirmed that the obtained starting crystals were in specification.

Figure 3:
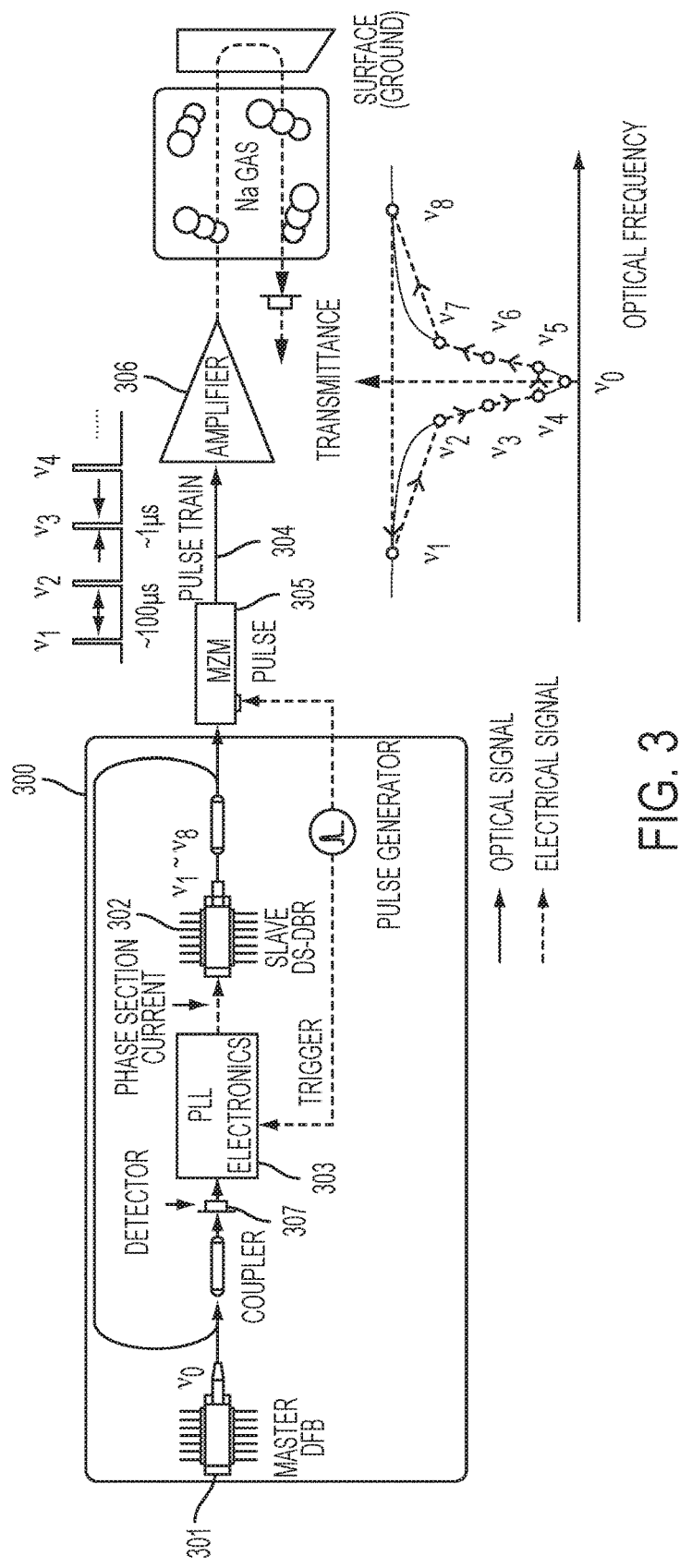
FIG. 3 is a schematic diagram of a fast wavelength tuning technology to perform spectroscopy, utilizing the Lidar instrument of FIG. 1, according to one embodiment consistent with the present invention.

In one embodiment, in order to perform spectroscopy, the wavelength of the Nd:YVO$_4$ laser 100, as described above, is temperature-tuned to the Na D$_2$ line (589.0 nm), and injection seed was used with a tunable Distributed FeedBack (DFB) laser diode 300 at 1066.55 nm (see FIG. 3). A precision and fast wavelength tuning technology 300 allows a wavelength-locked laser 301 (the CW laser 100 described above) to rapidly scan across an atomic/molecular (e.g., Na) absorption line at a user-selectable number of precise wavelengths for remote atmospheric spectroscopy measurements. In one embodiment of the present invention, the wavelength-locked laser is a master laser 301 that is wavelength-locked to the atomic (or molecular) line center by using a frequency modulation technique, limiting its frequency drift (one standard deviation) to 60 kHz at 0.8-sec averaging time over 72 hours.

In one embodiment, a second (i.e., slave) laser diode 302 is dynamically offset-locked to the master laser diode 301 by using an optical phase-locked loop (OPLL) 303, enabling precision fast-tuning of the slave laser 302 to and from any frequencies within a 40-GHz tuning range. For Na spectroscopy, the master laser 301 is 1178.4 nm that is doubled to 589.2 nm and wavelength-locked to a Na vapor cell. The offset-locked slave laser 302 is the tunable 1066.55 nm injection seeder 111 described above. The OPLL 303 suppresses any slow drift of the offset frequency, allowing the slave laser 302 to retain the absolute frequency stability of master laser 301. The frequency-stepped pulse train 304 is formed by external modulation through a Mach-Zehnder modulator (MZM) 305 and subsequent amplification by amplifier 306. The amplified pulse train is used to repeatedly measure at multiple points across the Na absorption line. The present invention satisfies stringent requirements for atmospheric gas sensing Lidars and enables other applications that require such well-controlled precision fast tuning.

In one embodiment, a space-qualified ultra-narrow (28 pm) optical filter, such as an atomic Na Faraday filter, may provide economic and performance benefits over the etalon filter, and along with the etalon filter, with 5-10 pm optical bandwidth, may enable some daytime Na Lidar observations.

In one embodiment, a space-flight-precursor photon-counting detector 307 is a 16-channel Photomultiplier Tube (PMT) with receiver electronics that has been space-qualified. The 16-channels are used as a photon-number-resolving "single" detector to provide the required full-spectroscopic Na lineshape waveform for recovering mesospheric temperature profiles. In one embodiment, a quantum-efficiency linear-mode hybrid photomultiplier and multi-channel silicon avalanche photodiodes are used. These alternate detectors may provide economic and performance benefits over the PMT.

In one embodiment, in testing, a 50 mW optical power 1178 nm DFB laser diode was temperature-tuned to the Na vapor $D_2$ line (589.0 nm). A commercial sodium vapor lamp was used to calibrate an optical spectrum analyzer. Sinusoidal current intensity (and thus, wavelength) modulation was applied at a 50 Hz frequency for real-time tuning across the Na vapor $D_2$ line. The Na vapor was heated to 110° C. using an oven, and the absorption spectrum was measured along with the calculated spectra.

In one embodiment, in testing, with a space-based 9 W laser optical output at 589.2 nm, a 0.8-meter optical receiver telescope and a photon-counting receiver, global mesospheric temperature profiles have been retrieved with the required temporal (~30 s), altitude (~1-2 km), temperature (~1K), and wind velocity (~1-5 m/s) resolution. The space-flight-precursor ground-based sodium Lidar of the present invention will allow direct verification of Lidar "Link" analysis (i.e., numerical estimate of the optical power, telescope aperture, detection system, and spectroscopic temperature recovery performance) by comparing experimental results to greatly improve extrapolation to a moving LEO space-based platform.

Accordingly, a laser transmitter to remotely measure Na by adapting existing Lidar technologies with space flight heritage has been developed. Wavelength tuning, injection seeding, resonator design and power scaling have been achieved on the laser transmitter of the present invention, based on diode-pumped Q-switched self-Raman c-cut Nd:YVO$_4$ laser with intra-cavity frequency doubling that produces multi-watt 589 nm wavelength output.

It should be emphasized that the above-described embodiments of the invention are merely possible examples of implementations set forth for a clear understanding of the principles of the invention. Variations and modifications may be made to the above-described embodiments of the invention without departing from the spirit and principles of the invention. All such modifications and variations are intended to be included herein within the scope of the invention and protected by the following claims.

What is claimed is:

1. A Lidar instrument comprising:
   a laser transmitter including:
   a continuous wave diode laser which emits laser beams at a predetermined wavelength, through mode matching lenses and a high reflective mirror to pump a c-cut Nd:YVO$_4$ crystal;
   a tunable seed continuous wave diode laser which emits laser beams through at least one mode matching lens, said laser beams which are redirected by a beam splitter to said c-cut Nd:YVO$_4$ crystal, such that the tunable seed laser acts as an injection seeder for said c-cut Nd:YVO$_4$ crystal to allow for tuning of the Nd:YVO$_4$ crystal which tunes said continuous wave diode laser to produce light at a wavelength of 1066 nm;
   wherein said tunable laser light after passing through said c-cut Nd:YVO$_4$ crystal self-Raman shifts to 1178 nm;
   wherein said continuous wave diode laser and said tunable seed continuous wave diode laser produce tunable laser light across the sodium $D_2$ absorption line; and
   wherein said c-cut Nd:YVO$_4$ crystal is a zig-zag crystal which supports multiple total internal reflections of optical wave propagation therethrough, and increases an optical path length greater than a physical dimension of said zig-zag crystal.

2. The Lidar instrument of claim 1, wherein said tunable laser light, after passing through said c-cut Nd:YVO$_4$ crystal, passes through one of a lithium triborate (LBO) crystal or a potassium titanyl phosphate (KTP) crystal which performs intra-cavity frequency doubling to output tunable laser light at 589 nm.

3. The Lidar instrument of claim 2, further comprising:
   an output coupler, operating at 1066 nm wavelength, through which said tunable laser light passes after passing through one of said lithium triborate crystal or said potassium titanyl phosphate crystal, and which outputs said tunable laser light at said 589 nm wavelength.

4. The Lidar instrument of claim 3, further comprising:
   an acousto-optic Q-switch which produces high-peak-power pulses to assist in said self-Raman shift to said 1178 nm wavelength in said c-cut Nd:YVO$_4$ crystal.

5. The Lidar instrument of claim 4, wherein a tuning range for a Na fluorescence spectrum is 4 GHz.

6. The Lidar instrument of claim 5, wherein said c-cut Nd:YVO$_4$ crystal is wrapped with an indium foil and bonded to a thermoelectric cooler (TEC) using a thermal phase change material (TPCM) as interface between the indium foil wrapped crystal and the TEC, for efficient cooling and thermal management.

7. The Lidar instrument of claim 1, wherein said zig-zag crystal is an even bounced vanadate slab that exhibits 10 mrad pyramidal error, and exhibits lasing pulses of 50 Hz, at 100 μs pump duration, and Q-switched lasing with $Cr^{4+}$:YAG as a saturable absorber.

8. The Lidar instrument of claim 7, wherein said zig zag crystal is prepared from two pieces of vanadate crystals that are diffusion bonded end-to-end to achieve a length of 40 nm.

9. The Lidar instrument of claim 8, wherein said diffusion bonding process is performed such that the crystalline axes are aligned to less than ±2 mrad.

10. The Lidar instrument of claim 3, wherein remote atmospheric spectroscopy is performed by using said continuous wave diode laser as a master laser diode, said master laser diode comprising:

a tunable Distributed FeedBack laser diode at 1178.4 nm, that is doubled to 589 nm and wavelength-locked to the sodium $D_2$ absorption line.

11. The Lidar instrument of claim 1, wherein said tunable continuous wave diode laser is a slave laser diode dynamically offset-locked to said master laser diode by using an optical phase-locked loop.

12. The Lidar instrument of claim 11, further comprising:
a Mach-Zehnder modulator; and
an amplifier;
wherein pulses from said slave laser diode are externally modulated by said Mach-Zehnder modulator to form a frequency-stepped pulse train which is amplified by said amplifier; and
wherein said amplified frequency-stepped pulse train is used to repeatedly measure at multiple points across the sodium $D_2$ absorption line.

13. The Lidar instrument of claim 12, further comprising:
a detector used as a full-spectroscopic sodium lineshape waveform to recover mesospheric temperature profiles.

14. A method of measuring range-resolved atmospheric sodium temperature profiles using a space-based Lidar instrument, comprising:
providing a continuous wave diode laser which emits laser beams at a predetermined wavelength through mode matching lenses and a high reflective mirror to pump a c-cut $Nd:YVO_4$ crystal;
providing a tunable seed continuous wave diode laser which emits laser beams through at least one mode matching lens;
redirecting said laser beams emitted from said tunable seed continuous wave diode laser using a beam splitter, to said c-cut $Nd:YVO_4$ crystal, such that the tunable seed laser acts as an injection seeder for said c-cut $Nd:YVO_4$ crystal to allow for tuning of the $Nd:YVO_4$ crystal which tunes said continuous wave diode laser to produce light at a wavelength of 1066 nm;
self-Raman shifting said tunable laser light after passing through said c-cut $Nd:YVO_4$ crystal, to 1178 nm;
wherein said continuous wave diode laser and said tunable seed continuous wave diode laser produce tunable laser light across the sodium $D_2$ absorption line; and wherein said c-cut $Nd:YVO_4$ crystal, is a zig-zag crystal, said zig-zag crystal supporting multiple total internal reflections of optical wave propagation therethrough, and increasing an optical path length greater than a physical dimension of said zig-zag crystal.

15. The method of claim 14, further comprising:
passing said tunable laser light through said c-cut $Nd:YVO_4$ crystal and then one of a lithium triborate (LBO) crystal or a potassium titanyl phosphate (KTP) crystal, in order to perform intra-cavity frequency doubling to output tunable laser light at 589 nm from an output coupler operating at 1066 nm wavelength.

16. The method of claim 15, further comprising:
preparing said zig zag crystal from two pieces of vanadate crystals that are diffusion bonded end-to-end to achieve a length of 40 nm; and
performing said diffusion bonding process such that the crystalline axes are aligned to less than ±2 mrad.

17. The method of claim 16, further comprising:
performing remote atmospheric spectroscopy using said continuous wave diode laser as a master laser diode, said master laser diode;
wherein a tunable Distributed FeedBack laser diode at 1178.4 nm, is doubled to 589 nm and wavelength-locked to a sodium $D_2$ absorption line; and
wherein said tunable continuous wave diode laser is a slave laser diode dynamically offset-locked to said master laser diode by using an optical phase-locked loop.

18. The method of claim 17, further comprising:
externally modulating pulses from said slave laser diode using a Mach-Zehnder modulator to form a frequency-stepped pulse train which is amplified by said amplifier; and
measuring repeatedly, using said amplified frequency-stepped pulse train, multiple points across the sodium absorption line.

19. The method of claim 18, further comprising:
using a detector as a full-spectroscopic sodium lineshape waveform to recover mesospheric temperature profiles.

* * * * *